US012801107B2

(12) United States Patent
Garg et al.

(10) Patent No.: US 12,801,107 B2
(45) **Date of Patent: *Nov. 17, 2026**

(54) SECURE REFRIGERATED BIN SYSTEMS

(71) Applicant: CareFusion 303, Inc., San Diego, CA (US)

(72) Inventors: Honey Garg, San Diego, CA (US); Magnus Felke, San Diego, CA (US); William Blackledge, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 386 days.

This patent is subject to a terminal disclaimer.

(21) Appl. No.: 18/377,262

(22) Filed: Oct. 5, 2023

(65) Prior Publication Data

US 2024/0036540 A1 Feb. 1, 2024

Related U.S. Application Data

(63) Continuation of application No. 17/867,558, filed on Jul. 18, 2022, now Pat. No. 11,789,420, which is a (Continued)

(51) Int. Cl.
*G05B 19/042* (2006.01)
*G16H 20/13* (2018.01)

(52) U.S. Cl.
CPC ........... *G05B 19/042* (2013.01); *G16H 20/13* (2018.01); *G05B 2219/2654* (2013.01)

(58) Field of Classification Search
None
See application file for complete search history.

(56) References Cited

U.S. PATENT DOCUMENTS

| | | | |
|---|---|---|---|
| 5,572,873 | A | 11/1996 | Lavigne et al. |
| 6,839,304 | B2 | 1/2005 | Niemiec et al. |

(Continued)

FOREIGN PATENT DOCUMENTS

| | | | |
|---|---|---|---|
| AU | 2011338579 | A1 | 7/2013 |
| CN | 205279567 | U | 6/2016 |

(Continued)

OTHER PUBLICATIONS

European Office Action for Application No. 19731109.5, dated Feb. 8, 2024, 11 pages.

(Continued)

*Primary Examiner* — David Earl Ogg
(74) *Attorney, Agent, or Firm* — MASCHOFF BRENNAN

(57) ABSTRACT

Disclosed are systems and methods for managing secure refrigerated bin systems. A system receives a request to access a respective compartment of a plurality of compartments in a dispensing device. Responsive to receiving the access request and identifying one or more medications in the respective compartment, a safe temperature range specific to the identified one or more medications is determined, and a temperature of the respective compartment is determined using a respective temperature sensor of the respective compartment. The system determines whether the determined temperature of the respective compartment is within the safe temperature range of the identified one or more medications causes an alert to be displayed when the determined temperature of the respective compartment is outside of the safe temperature range of the identified one or more medications.

22 Claims, 5 Drawing Sheets

Related U.S. Application Data continuation of application No. 16/428,907, filed on May 31, 2019, now Pat. No. 11,392,101.

(60) Provisional application No. 62/679,745, filed on Jun. 1, 2018.

(56) References Cited

U.S. PATENT DOCUMENTS

| | | | | |
|---|---|---|---|---|
| 7,775,056 | B2 | 8/2010 | Lowenstein | |
| 8,756,122 | B2 | 6/2014 | Lowenstein | |
| 8,773,270 | B2 | 7/2014 | Paydar et al. | |
| 9,574,817 | B2 | 2/2017 | Cloyd | |
| 9,579,245 | B2 | 2/2017 | Larkner et al. | |
| 10,134,099 | B2 | 11/2018 | Lowenstein | |
| 10,663,218 | B2 | 5/2020 | Belligundu | |
| 10,823,499 | B2 * | 11/2020 | Manning | F25D 29/00 |
| 2003/0007421 | A1 | 1/2003 | Niemiec et al. | |
| 2004/0108795 | A1 | 6/2004 | Meek | |
| 2009/0132090 | A1 | 5/2009 | Kaczmarz | |
| 2010/0275625 | A1 | 11/2010 | Lowenstein | |
| 2010/0300130 | A1 | 12/2010 | Shoenfeld et al. | |
| 2012/0209763 | A1 | 8/2012 | Zabbatino | |
| 2013/0253700 | A1 | 9/2013 | Carson | |
| 2014/0165614 | A1 | 6/2014 | Manning et al. | |
| 2014/0244289 | A1 | 8/2014 | Lowenstein | |
| 2014/0338378 | A1 * | 11/2014 | Paradissis | G07F 9/002 62/126 |
| 2016/0074284 | A1 | 3/2016 | Despa | |
| 2016/0132662 | A1 * | 5/2016 | Paradissis | G07F 9/001 700/244 |
| 2016/0193966 | A1 | 7/2016 | Lem | |
| 2017/0109480 | A1 * | 4/2017 | Vahlberg | A61J 7/0084 |
| 2017/0258658 | A1 | 9/2017 | Larkner | |
| 2019/0154329 | A1 | 5/2019 | Belligundu | |

FOREIGN PATENT DOCUMENTS

| | | | |
|---|---|---|---|
| CN | 107625312 | A | 1/2018 |
| WO | WO-2019079468 | A1 | 4/2019 |
| WO | WO-2019152803 | A1 | 8/2019 |

OTHER PUBLICATIONS

Mexican Office Action for Application No. MX/a/2020/012000, dated Oct. 26, 2023, 4 pages including English memo.

Australian Office Action for Application No. 2019276564, dated Apr. 19, 2024, 4 pages.

Compartmental Access Refrigerator Operation Manual, Helmer Scientific, Part No. 360178-A/C, initial release date Jan. 26, 2015, 29 pages.

Indian Office Action for Application No. 202037056397, dated Jun. 28, 2022, 7 pages.

International Search Report and Written Opinion for Application No. PCT/US2019/035041, dated Sep. 10, 2019, 17 pages.

Korean Office Action for Application No. 10-2020-7035668, dated Jul. 15, 2022, 5 pages including English translation.

Refrigerator Operation Manual i.Series® and Horizon Series™—Undercounter, Helmer Scientific, Part No. 360374/C, initial release date Dec. 7, 2016, 28 pages.

Refrigerator Operation Manual i.Series® and Horizon Series™—Upright, Helmer Scientific, Part No. 360372/ Rev B, initial release date Nov. 3, 2016, 30 pages.

Singapore Written Opinion for Application No. 11202011453Q, dated Sep. 16, 2022, 8 pages.

Australian Office Action for Application No. 2019276564, dated Aug. 15, 2024, 5 pages.

Canadian Office Action for Application No. 3101750, dated Sep. 3, 2024, 6 pages.

United Arab Emirates Office Action for Application No. P6001706/2020, dated Sep. 6, 2024, 9 pages.

European Office Action for Application No. 19731109.5, dated Feb. 26, 2025, 5 pages.

Canadian Office Action for Application No. 3101750, dated Oct. 3, 2023, 6 pages.

Chinese Office Action for Application No. 201980036641.3, dated Sep. 25, 2023, 20 pages including translation.

* cited by examiner

SECURE REFRIGERATED BIN SYSTEMS

CROSS-REFERENCE TO RELATED APPLICATIONS

This application is a continuation of application Ser. No. 17/867,558, filed on Jul. 18, 2022, now U.S. Pat. No. 11,789,420, which is a continuation of application Ser. No. 16/428,907, filed on May 31, 2019, now U.S. Pat. No. 11,392,101, which claims the benefit of U.S. Provisional Application No. 62/679,745, filed on Jun. 1, 2018, the entirety of each of which is incorporated herein by reference for all purposes.

BACKGROUND

The stability and preservation of most medications are subject to strict temperature requirements. The active chemicals in a medication can change in molecular form when exposed to different temperatures, resulting in decomposition of the medication, making the medication less potent or result in new or different effects. Medications designated to be refrigerated represent some of the most clinically necessary, complex and costly medications available, including oncology drugs and injectable biologics.

In the medical field, refrigerated medications are often stored in auxiliary refrigeration units. Current auxiliary refrigeration units, however, often store medications in a comingled fashion. In this regard, all medications are subject to the same temperature settings, despite having different temperature requirements. Moreover, access to one medication leads to access to all medications and, under these circumstances, a current temperature setting for the refrigeration unit may be suitable to some of the medications stored inside, but damaging to others. Accordingly, medications may be stored across various units, each having different storage and environmental characteristics. Disparate medication management processes and technologies for ambient and refrigerated medications have led to inefficiencies, increased cost, treatment delays, patient harm, and even death. Thus, there is a need to provide a more efficient method of managing and administering refrigerated medications.

BRIEF DESCRIPTION OF THE DRAWINGS

The accompanying drawings, which are included to provide further understanding and are incorporated in and constitute a part of this specification, illustrate disclosed implementations and together with the description serve to explain the principles of the disclosed implementations. In the drawings.

DETAILED DESCRIPTION

In the following detailed description, numerous specific details are set forth to provide a full understanding of the present disclosure. It will be apparent, however, to one ordinarily skilled in the art that implementations of the present disclosure may be practiced without some of the specific details. In other instances, well-known structures and techniques have not been shown in detail so as not to obscure the disclosure. In the referenced drawings, like numbered elements are the same or essentially similar. Reference numbers may have letter suffixes appended to indicate separate instances of a common element while being referred to generically by the same number without a suffix letter.

According to some implementations, a system disclosed herein may include an automated dispensing cabinet (ADC) that includes an integrated medical-grade refrigerator. According to some implementations, the refrigerated ADC includes secure locking bins that unlock when remotely accessed via a remote control system. The bins may be controlled by a remote manager that takes into account various parameters, including an authorization level of a caregiver logging into the system, the types of medications stored inside, and the temperature characteristics of the particular bin to be accessed.

By the use of this technology, a high level of security can be extended to refrigerated medications ("meds"). This system may innovate delivery of care by enabling clinical workflow efficiency, waste reduction, and capability to meet state, federal and safety organization guidelines around refrigerated medication management at the point of use for acute care and non-acute care settings. In this regard, the technology disclosed herein may further support medication safety by properly securing and storing refrigerated medications and improving medication availability, help prevent diversion and its associated risk to medication safety and patient care, and help store sensitive and expensive medications and vaccines at appropriate conditions to help improve safety and address regulatory risks.

Figure 1:
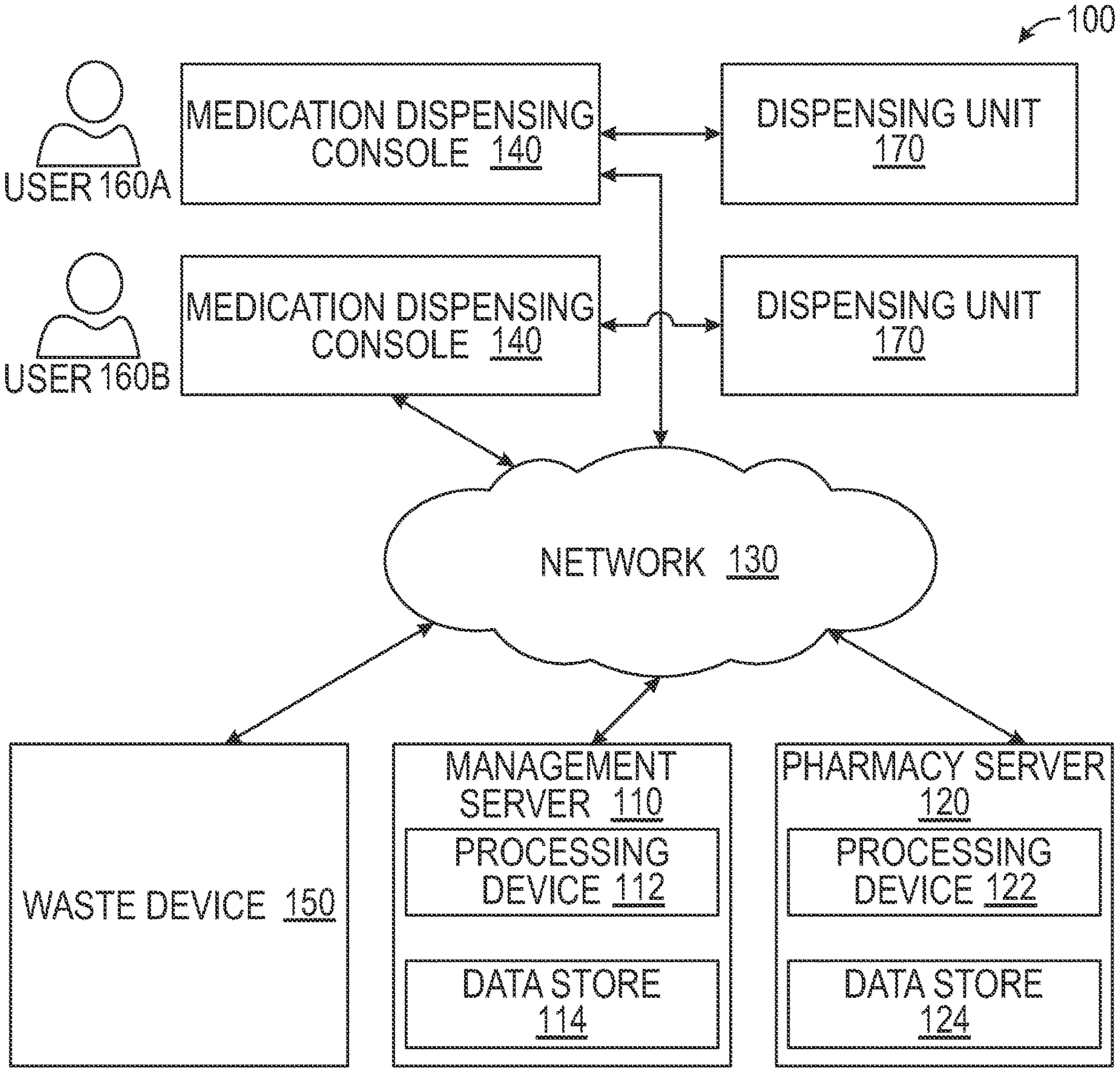
FIG. 1 illustrates a schematic diagram of an example system for providing secure refrigerated bin systems for medications, in accordance with one or more implementations.

FIG. 1 illustrates a schematic diagram of an example system 100 for providing secure refrigerated bin systems for medications, in accordance with one or more implementations of the subject technology. Not all of the depicted components may be required, however, and one or more implementations may include additional components not shown in the figure. Variations in the arrangement and type of the components may be made without departing from the spirit or scope of the claims as set forth herein. Additional, different or fewer components may be provided.

System 100 may be a hospital network, a network associated with a portion of a hospital or other healthcare facility, a network that includes multiple hospitals and/or other healthcare facilities. System 100 may include a number of medical devices, such as one or more medication dispensing consoles 140, and/or one or more waste devices 150, that may be communicably coupled to one another and to one or more of a management server 110 and/or a pharmacy server 120, such as by the network 130. One or more dispensing units 170 may be communicably coupled to one or more medication dispensing consoles 140, for example by direct Ethernet connection. In other implementations, dispensing units 170 may communicate via network 130. In addition, there may be a number of other devices connected to the network 130, such as additional medical devices, additional servers, computing devices, mobile devices, etc.

The network 130 may be a public communication network (such as the Internet, cellular data network, dialup modems over a telephone network) or a private communications network (such as private local area network ("LAN"), leased lines). The network 130 may also include, but is not limited to, any one or more of the following network topologies, including a bus network, a star network, a ring network, a mesh network, a star-bus network, a tree or hierarchical network, and the like. The connections may be wired or wireless.

The medication dispensing consoles 140 may be devices that store and dispense medications, such as at a nurse's station. Exemplary users 160A and 160B of the system may be nurses, doctors, or other healthcare professionals that interface with medication dispensing console 140 to retrieve medications for administration to patients. In some implementations, the medication dispensing consoles 140 are configured to automatically monitor dispense events (e.g., using one or more sensors) to obtain information regarding each dispense of medication. In one or more implementations, one or more of the medication dispensing consoles 140 may be configurable for direct communication with other dispensing consoles and other medical devices and databases via network 130. The waste devices 150 may be devices that accept and store wasted medications, e.g., excess medications, from healthcare professionals and track the amount of medications wasted by healthcare professionals.

In one or more implementations, one or more of the medication dispensing devices 140 and/or the waste devices 150 may include a processing device, such as a processor, and a memory. The processing device executes computer instructions stored in the memory, such as to implement one or more processes employing principles disclosed herein. In one or more examples, the computer instructions may be stored on a non-transitory computer-readable medium. In one or more implementations, a medication dispensing device 140 and a waste device 150 may be combined in a single device.

In one example, the management server 110 and/or the pharmacy server 120 may be single computing devices such as computer servers and/or the management server 110 and the pharmacy server 120 may be a single machine. In another example, the management server 110 and/or the pharmacy server 120 may represent one or more separate computing devices (such as a cloud of computers and/or a distributed system) that are communicatively coupled, such as communicatively coupled over the network 130, that collectively, or individually, perform one or more server-side functions. In this example, the one or more computing devices of the management server 110 and/or the pharmacy server 120 may be geographically collocated and/or disparately located. The management server 110 and/or pharmacy server 120 may be coupled with various databases, storage services, or other computing devices.

In one or more implementations, the management server 110 includes a processing device 112 and a data store 114. The processing device 112 executes computer instructions stored in the data store 114, such as to implement one or more processes employing principles disclosed herein. In one or more examples, the data store 114 may store the computer instructions on a non-transitory computer-readable medium. In one or more implementations, the pharmacy server 120 includes a processing device 122 and a data store 124. The processing device 122 executes computer instructions stored in the data store 124, such as to implement one or more processes employing principles disclosed herein. In one or more examples, the data store 124 may store the computer instructions on a non-transitory computer-readable medium. In one or more implementations, the management server 110, the pharmacy server 120, the medication dispensing console 140 and/or the dispensing unit 170 may be, or may include, the electronic system 8000 discussed below with respect to FIG. 5.

In operation, the system 100 and/or one or more of the medication dispensing consoles 140 and dispensing units 170 may implement one or more aspects of a secured refrigerated locked bin system or other system employing principles disclosed herein, such as by performing one or more of the example processes that are discussed herein.

Figure 2:
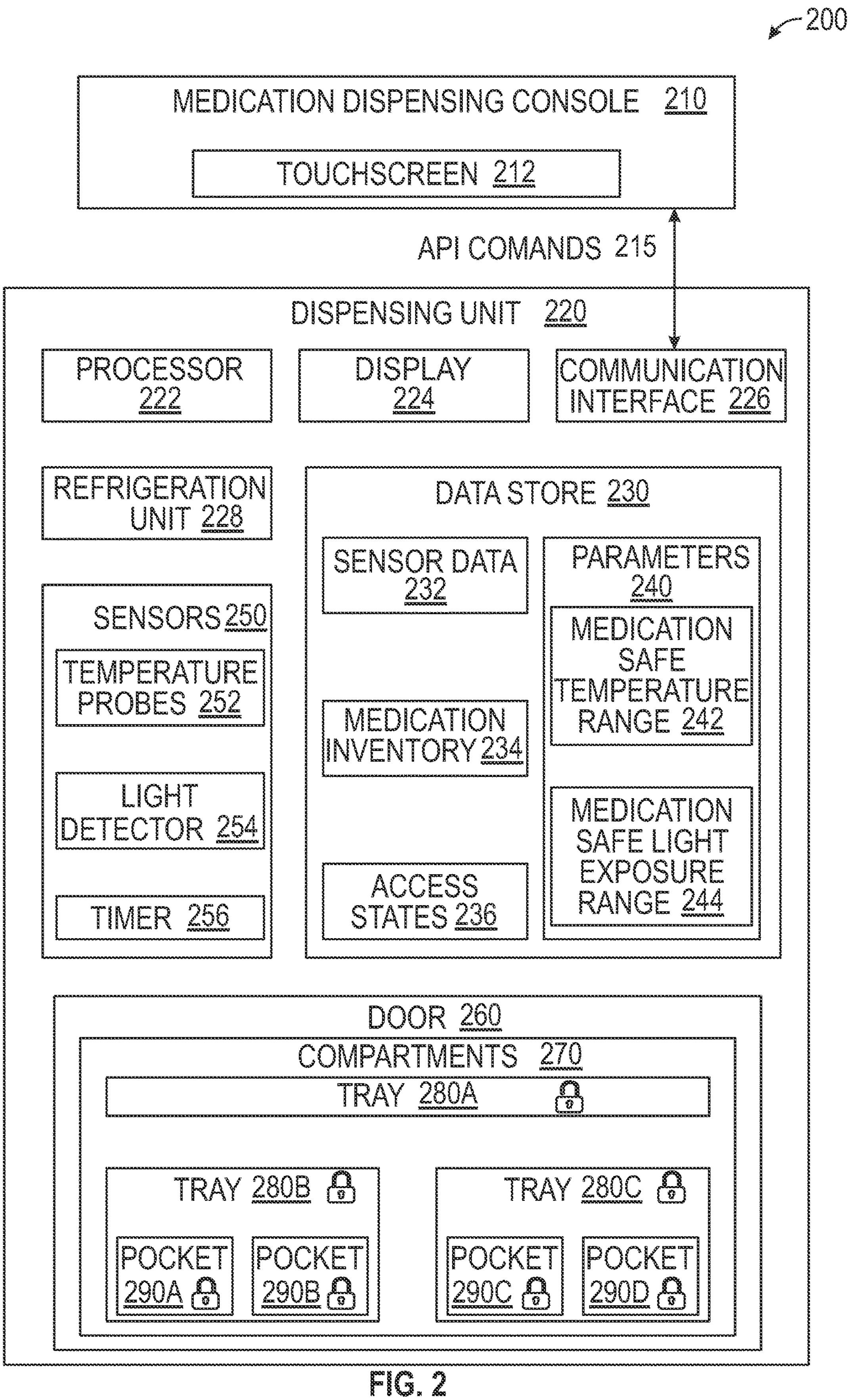
FIG. 2 illustrates a schematic diagram of an example system including a dispensing unit for providing secure refrigerated bins, in accordance with one or more implementations.

FIG. 2 illustrates a schematic diagram of an example system 200 including a dispensing unit 220 for providing secure refrigerated bins, in accordance with one or more implementations of the subject technology. Not all of the depicted components may be required, however, and one or more implementations may include additional components not shown in the figure. Variations in the arrangement and type of the components may be made without departing from the spirit or scope of the claims as set forth herein. Additional, different or fewer components may be provided. With respect to FIG. 2, medication dispensing console 210 may correspond to medication dispensing console 140 from FIG. 1, and dispensing unit 220 may correspond to dispensing unit 170 from FIG. 1.

As shown in FIG. 2, dispensing unit 220 may include several components, including processor 222, display 224, communication interface 226, refrigeration unit 228, data store 230, sensors 250, and door 260. Door 260 may include compartments 270. Compartments 270 may include tray 280A, tray 280B, and tray 280C. Tray 280B may include pocket 290A and pocket 290B, and tray 280C may include pocket 290C and pocket 290D. Data store 230 may include sensor data 232, medication inventory 234, access states 236, and parameters 240. Parameters 240 may include medication safe temperature range 242 and medication safe light exposure range 244, for example, for one or more compartments 270, trays 280, pockets 290, and/or the dispensing unit 220 as a whole. Sensors 250 may include temperature probes 252, light detector 254, and timer 256.

Processor 222 may be any general purpose or specialized processor, including a microprocessor, microcontroller, field-programmable gate array (FPGA), application-specific integrated circuit (ASIC), or any other combination of hardware, firmware, and software. Processor 222 may execute computer instructions, for example instructions stored in data store 230, to respond to application program interface (API) commands 215, which may be received via communication interface 226. Communication interface 226 may be an Ethernet wired networking card, a wireless card using Wi-Fi or Bluetooth, or any other communications interface.

For example, referring back to FIG. 1, user 160A may utilize medication dispensing console 140 to request a particular medication to be retrieved. Turning back to FIG. 2, user 160A may, for example, utilize touchscreen 212 to select the particular medication. This action may trigger one or more API commands 215 to be sent from medication dispensing console 210 to dispensing unit 220. Dispensing unit 220 may then respond to API commands 215 accordingly to grant access to the requested medication, as described further in conjunction with FIG. 3 below.

As shown in FIG. 2, dispensing unit 220 includes several components for controlling the condition of door 260 and compartments 270. Refrigeration unit 228 may be a compressor or other suitable device for controlling the ambient temperature in compartments 270. Sensors 250 may records various states of compartments 270, such as ambient temperature via temperature probes 252, and light via light detector 254. Sensors 250 may also detect the lock state of each lockable compartment in dispensing unit 220, including door 260 and compartments 270. In some implementations, one or more compartments may be unsecured, such as tray 280A. In this case, the lock state of the compartment, such as tray 280A, may be always unlocked.

As shown in FIG. 2, dispensing unit 220 may also maintain several groups of data in data store 230. Sensor data 232 may include data recorded by sensors 250, and may maintain a log of sensor data over time. Medication inventory 234 may track the medications stored in each individual compartment within compartments 270. Thus, medication inventory 234 may include the contents of tray 280A, tray 280B including pocket 290A and 290B, and tray 280C including pocket 290C and pocket 290D. Access states 236 may track the lock and unlock state of door 260 and compartments 270, which may be maintained and logged over time. Parameters 240 may include one or more parameters that indicate whether particular medications are safe and effective to use. For example, medication safe temperature range 242 may indicate the temperature ranges that particular medications should be stored to maintain safety and efficacy. Similarly, medication safe light exposure range 244 may indicate a safe range of light exposure before particular medications become unsafe or ineffective. Some of the data in data store 230, such as medication inventory 234 and parameters 240, may be initially populated from data retrieved from a centralized management location, such as management server 110 and/or pharmacy server 120.

While compartments 270 in FIG. 2 is shown to have a single unsecured tray 280A and two secured trays 280B and 280C with respective pockets 290A-290B and 290C-290D, the specific configuration of compartments 270 can be flexibly chosen according to use case requirements and available space. Dispensing unit 220 can be configured as a large tower refrigerator or a compact refrigerator, and compartments can be arranged according to site requirements. Compartments may be nested as many levels as desired, and multiple trays may be arranged horizontally and vertically, with or without pockets. Compartments may also be configured as long depth compartments that slide in and out. Further, while medication dispensing console 210 and dispensing unit 220 are shown as separate in FIG. 2, other implementations may provide a single integrated console and refrigerated dispensing unit.

Dispensing unit 220 may also include additional components not shown in FIG. 2. For example, a battery backup may be provided to enable the dispensing unit 220 to continue operating during power loss. Further, emergency manual override locks may be provided to provide access to any locked devices, such as door 260 and compartments 270. Access to particular trays and pockets via manual locks may be recorded into data store 230, and these records may be transferred to medication dispensing console 210 to synchronize with a centralized inventory management system, e.g. at management server 110 or pharmacy server 120.

Figure 3A:
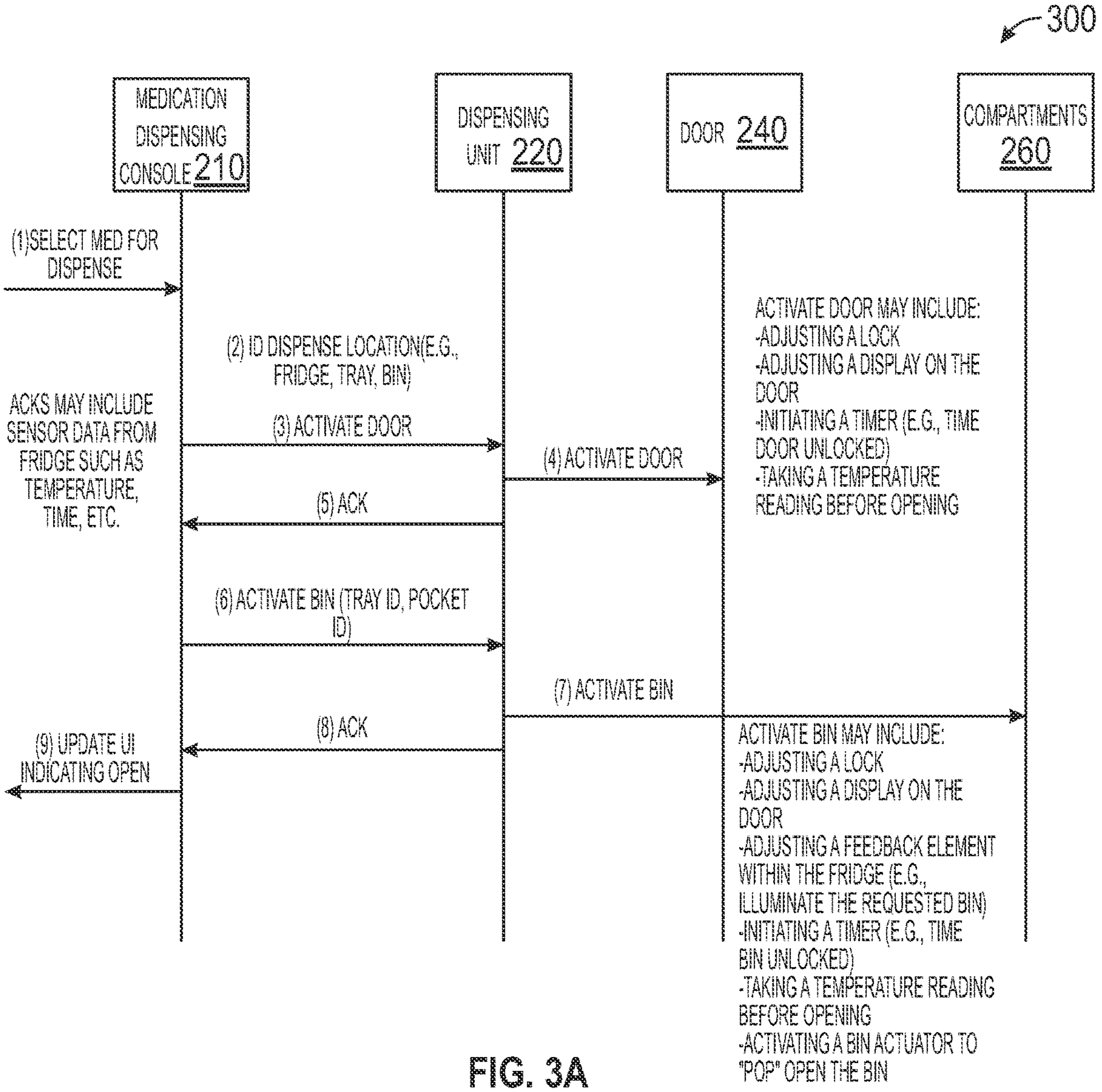
FIG. 3A illustrates a message flow diagram for requesting access to a refrigerated medication using a system providing secure refrigerated bin access, in accordance with one or more implementations.

FIG. 3A illustrates a message flow diagram 300 for requesting access to a refrigerated medication using a system providing secure refrigerated bin access, in accordance with one or more implementations. With respect to FIG. 3A, medication dispensing console 210, dispensing unit 220, door 260 and compartments 270 may correspond to the same elements from FIG. 2.

At step (1), referring to FIG. 1, user 160A may select a medication for dispensing. For example, user 160A may login to medication dispensing console 140, select a registered patient, and then select a prescribed medication for administration. For example, touchscreen 212 of FIG. 2 may display a user interface allowing user 160A to select the medication. The user interface may appear similar to the example user interface of touchscreen 312 shown in FIG. 3B.

According to various implementations, access to medication is determined, at least in part, based on access privileges of the caregiver accessing the dispensing unit. Prior to selecting a medication for dispensing, user 160A (e.g., a caregiver) may log in to the system using one or more user credentials, key card, or bio-identification device. For example, the user interface may prompt the user to enter a password, swipe a badge, or provide a fingerprint scan before accessing the device. In some implementations, an intelligent radio frequency (RF) computer chip is incorporated into a user's badge or wristband that provides a unique, or programmed response with a passive RF transponder located within dispensing unit 220 or at or near display 224 or communication interface 226. Each badge interacts with signals of the transponder in a unique way, the unique interaction representing an assigned code for the badge or wristband. Accordingly, manual steps and some of the "human factor" are removed from the process of identifying the patient and caregiver. When a badge or wristband is held near the transponder or, in some implementations, when an individual wearing a badge or wristband having such a circuit enters a predetermined area near or where the transmitter/receiver is located, the electronic circuit in the badge or wristband may interact with signals emitted by the transmitter without any further positive action on the part of the user. This interaction may be sensed by the receiver, which may be capable of determining the identity of the badge or wristband from the interaction of the electronic circuit with the emitted signals without active involvement from the user. In some implementations, dispensing unit may sense the interaction and provide a signal representative of the sensed interaction to an external computer or other processor that has been programmed or otherwise configured to determine the identity of the individual associated with that particular badge or wristband (e.g., via network 130). The external computer or processor may provide dispensing unit 220 with authorization information that may include the access privileges for that particular individual.

Figure 3B:
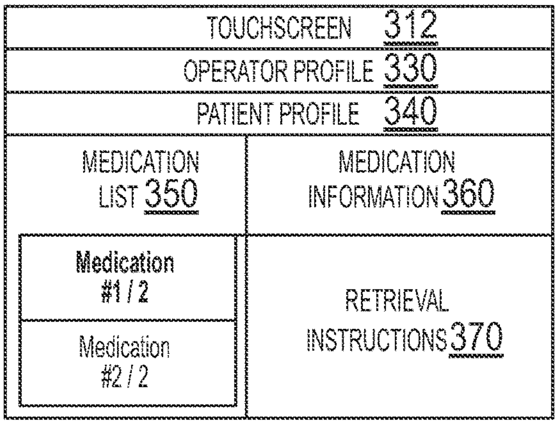
FIG. 3B and FIG. 3C illustrate example user interfaces displayed on a medication dispensing console and a dispensing unit, respectively, in accordance with one or more implementations.

As shown in FIG. 3B, the user interface may include operator profile 330 for user 160A, patient profile 340 for the selected patient, and medication list 350 for selecting a prescribed medication. As shown in FIG. 3B, Medication #1/2 is selected. Once selected, medication information 360 may be updated, such as by displaying drug name and dosage, whereas retrieval instructions 370 may direct user 160A to the specific dispensing unit, tray, pocket, bin, or other compartment to find the selected medication.

Note that medication list 350 may maintain a list of medications in a specific order. For example, this order may be medically important to maintain when administrating to the patient. In this case, user 160A may be prevented from selecting medications in medication list 350 out of order, and the next medication may be selected automatically from medication list 350.

Once a particular medication is selected, flow diagram 300 proceeds to step (2), or identifying a dispense location. For example, management server 110 and/or pharmacy server 120 may be contacted to determine an inventory of dispensing unit 170. Alternatively, dispensing unit 170 may be directly queried for its contents, if known. Once medication inventory 234 is known, then the specific compartment within compartments 270 can be identified as containing the requested medication. As discussed above, this may be displayed as retrieval instructions 370. For example, retrieval instructions 370 may state, "Remove 1 INJECTION from BDFridgel, Bin 2.1, Pocket 1." This may correspond to dispensing unit 220 ("BDFridgel"), Tray 280B ("Bin 2.1", using column/row convention), Pocket 290A ("Pocket 1", or the first pocket from the left). Thus, user 160A knows to retrieve one injection from pocket 290A.

At step (3), a message to activate door 260 is sent. As shown in flow diagram 300, this is accomplished by medication dispensing console 210 sending a message to dispensing unit 220, for example by sending API commands 215, as shown in FIG. 2.

Figure 3C:
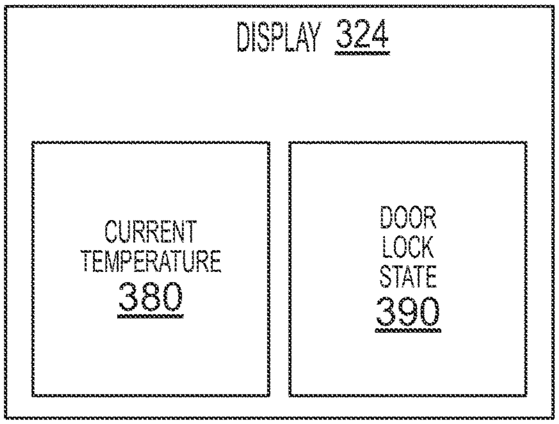

At step (4), dispensing unit 220 instructs door 260 to activate itself. Activation may include, for example, electrically unlocking door 260 to change an access state from locked to unlocked. Activation may also trigger several other actions, such as triggering timer 256 to measure a time period while door 260 is open, or updating a display. For example, FIG. 3C illustrates an example user interface displayed on a dispensing unit. As shown on display 324, which may correspond to display 224 from FIG. 2, a door lock state 390 may be updated in response to the activation, for example by displaying an unlocked padlock icon. Current temperature 380 may also be maintained according to the sensed ambient temperature. Door 260 activation may also include taking a temperature reading before opening the door.

At step (5), dispensing unit 220 sends an acknowledgement (ACK) back to medication dispensing console 210, indicating that the activation of door 260 was successful.

At step (6), medication dispensing console 210 sends a new API command to dispensing unit 220 to activate the requested compartment—or "Bin 2.1, Pocket 1" corresponding to pocket 290A.

At step (7), dispensing unit 220 receives the request and activates the requested compartment. As with activating door 260, activating the requested compartment may trigger several different actions. For example, the access state may change from locked to unlocked. In this example, since there are other locked compartments in the path of the requested compartment, the other locked compartments may also be unlocked as well. For example, tray 280B may be unlocked as well to provide access to pocket 290A. Generally, any other locked compartments in the path of the requested compartment may be unlocked to provide access. Timer 256 may be triggered to measure a period of time that the compartment is unlocked. Sensors 250 may be triggered to update their readings, such as taking a temperature reading before opening the requested compartment. Another triggered action may be updating a display (e.g., a user interface displayed on the dispensing unit). For example, by displaying an unlocked padlock icon for pocket 290A.

To facilitate identification, one or more feedback elements may be triggered, such as illuminating a light, to identify the compartment (pocket 290A) to user 160A. One or more mechanical elements may also be triggered to facilitate access to the requested compartment. For example, if the compartment has a lid, the lid may be popped up using an actuator. If the compartment is in a deep drawer, the drawer may push out fully, or alternatively to the appropriate depth to provide access to the compartment. Thus, the compartment may be illuminated, opened, moved, or otherwise made accessible to the user.

At step (8), dispensing unit 220 sends an acknowledgement (ACK) back to medication dispensing console 210, indicating that the activation of pocket 290A was successful.

At step (9), the user interface is updated to indicate that access is granted. For example, door lock state 390 may be updated in display 324 of FIG. 3C.

At this point, access to the requested medication is granted, and user 160A may then open door 260 to access the medication from pocket 290A of compartments 270. After confirmation of medication removal, all of the compartments may be manually locked or alternatively automatically locked if supported, and door 260 may close and lock. For example, user 160A may scan a barcode on the removed medication at medication dispensing console 210 to confirm removal. Alternatively, RFID tags or other tracking methods may be utilized. In the case of manual locking, door 260 may only close and lock after compartments 270 are confirmed to be locked and secured.

In some cases, it may be necessary to retrieve multiple medications from the same dispensing unit. In this case, the flow diagram 300 may be modified by maintaining a lock state of door 260 as unlocked until all medications are retrieved, for convenience. More specifically, dispensing unit 210 may maintain door 260 as unlocked until a final command is received in an ordered list of commands retrieved from medication dispensing console 210.

In some implementations, medications in one compartment 270, tray 280A-C, or pocket 290A-D may have different acceptable temperature ranges than medications in another compartment 270, tray 280A-C, or pocket 290A-D. For example, the entire dispensing unit 220 may be cooled to a particular temperature (e.g., 50 degrees F.), while one or more medications in tray 280A may have a recommended or acceptable temperature storage range of 35-45 degrees F. Thus, the medications in tray 280A would be out of the recommended or acceptable temperature storage range and may be considered spoiled or unfit for use. Accordingly, the dispensing unit 210 may prevent tray 280A from unlocking or opening, even with proper authentication of the user 160A, 160B. In particular, all compartments 270, trays 280A-C, and pockets 290A-D containing medications having recommended or acceptable temperature ranges that include the temperature of the dispensing unit 210 may be openable upon proper authentication, while any compartments 270, trays 280A-C, and pockets 290A-D containing medications having recommended or acceptable temperature ranges that do not include the temperature of the dispensing unit 210 will remain locked or closed in order to prevent access to the medications that have been exposed to adverse temperatures.

Similarly, temperature ranges may vary within the dispensing unit 210, such that tray 280A may be cooled to one temperature (e.g., 50 degrees F.) while tray 280B may be cooled to a different temperature (e.g., 45 degrees F.). Here, the temperature of each tray 280A, 280B may be taken upon the signal to activate that tray 280A, 280B and unlocking or opening of that tray 280A, 280B may be prevented if the temperature is outside of the acceptable or recommended temperature range for the medications within. In addition to locking or preventing access to compartments 270, trays 280A-C, and pockets 290A-D containing medications having recommended or acceptable temperature ranges that have been exceeded, an alarm or alert may be displayed and/or sent to an appropriate authority so that the compromised medications may be removed and disposed of. In some implementations the door 260 may remain locked or closed if any of the compartments 270, trays 280A-C, and pockets 290A-D contain medications having recommended or acceptable temperature ranges that have been exceeded, thus preventing access to all medications until the compromised medications have been removed.

Further, any of the above described actions may be provided on the basis of light exposure as well. For example, medications may have different recommended or acceptable light exposure ranges, where some medications need to be kept essentially in the dark or cannot be exposed to ultraviolet light. Similarly to the temperature readings, light detectors 254 may be associated with any of door 260, compartment 270, trays 280A-C, and pockets 290A-D, such that detected light exposure outside of the acceptable range for even one medication stored within causes the respective door 260, compartment 270, trays 280A-C, and pockets 290A-D to remain locked or closed.

In addition, timers 256 may be used to measure or detect the duration of exposure of medications within a door 260, compartment 270, trays 280A-C, and/or pockets 290A-D. For example, a medication in tray 280C may have been exposed to an out of acceptable range temperature or light radiation for just a few seconds, which may be within an acceptable threshold of time for that medication. Accordingly, the dispensing unit 220 may provide for access to that medication by opening tray 280C upon proper authentication of the user 160A, 160B.

Figure 4:
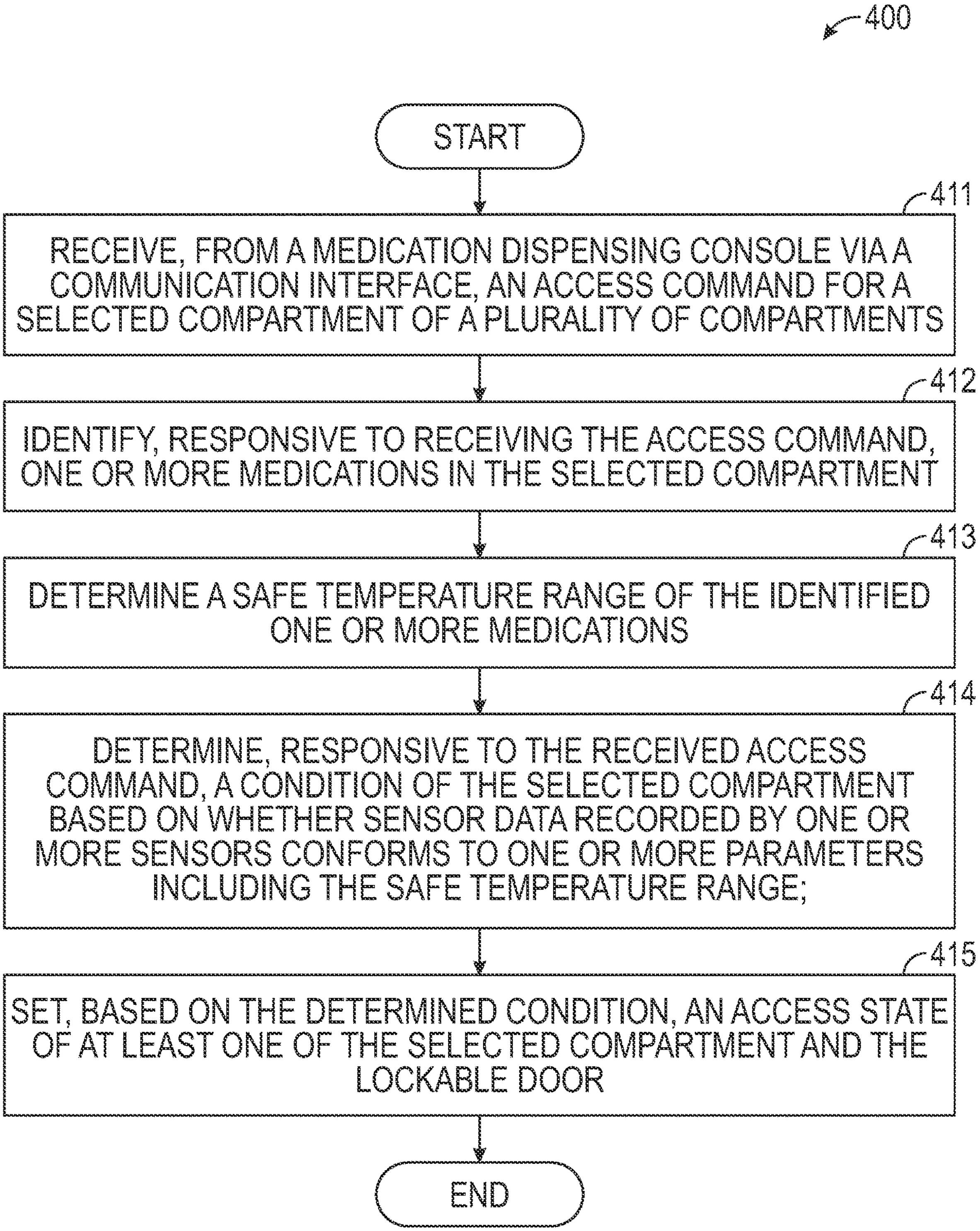
FIG. 4 illustrates a flowchart for an example process for requesting access to a refrigerated medication using a system providing secure refrigerated bin systems, in accordance with one or more implementations.

FIG. 4 illustrates a flowchart for an example process 400 for requesting access to a refrigerated medication using a system providing secure refrigerated bin systems, in accordance with one or more implementations. One or more blocks of FIG. 4 may be executed by a computing system, such as processor 222. Similarly, a non-transitory machine-readable medium may include machine-executable instructions thereon that, when executed by a computer or machine, perform the blocks of FIG. 4. The steps of process 400 may be implemented as hardware/firmware or software.

In block 411, referring to FIG. 2, processor 222 receives, from medication dispensing console 210 via communication interface 226, an access command or API commands 215 for a selected compartment of compartments 270. Using the same example illustrated above with flow diagram 300, processor 222 may receive an access command for "Bin 2.1, Pocket 1," or pocket 290A. As discussed above, the compartment may be selected by providing a user interface on medication dispensing console 210 to select a medication and identify the compartment that contains the medication.

In block 412, referring to FIG. 2, processor 222 identifies, responsive to receiving the access command, one or more medications in the selected compartment. For example, processor 222 may lookup medication inventory 234 in data store 230 to identify the one or more medications.

In block 413, referring to FIG. 2, processor 222 determines a safe temperature range of the identified one or more medications from block 412. For example, processor 222 may lookup medication safe temperature range 242 in parameters 240, which may include safe temperature range information for various medications including those in medication inventory 234. Based on the identified medications in the selected compartment as determined in block 412, the safe temperature range for those identified medications can therefore be determined. Further, each compartment 270, tray 280A-C, and/or pocket 290A-D may store different medication(s) and the safe temperature/light exposure range for those medications stored within may be determined to provide a check on a per medication basis.

In block 414, referring to FIG. 2, processor 222 determines, responsive to the received access command, a condition of the selected compartment based on whether sensor data 232 recorded by sensors 250 conforms to parameters 240 including the safe temperature range 242 for the identified medications. For example, if the temperatures recorded by temperature probes 252 in sensor data 232 are within in the medication safe temperature range 242 and any recorded light exposure (e.g. by using light detector 254 or timer 256 to record time periods door 260 is open) is within medication safe light exposure range 244, then the condition can be determined to be "safe and effective." However, if the recorded temperatures or light exposure are at any time outside the safe ranges, then a determination is made whether the condition remains "safe and effective" (e.g., the exceeded temperature or light exposure was less than a threshold of 30 seconds). For example, heuristic analysis or other methodologies can be used to analyze sensor data 232 and make the determination.

In block 415, referring to FIG. 2, processor 222 sets, based on the determined condition from block 414, an access state of at least one of the selected compartment and door 260. For example, if the condition is "safe and effective," then the access state of door 260, tray 280B, and pocket 290A may all be set to unlocked. On the other hand, of the condition is "unsafe" or "ineffective," then pocket 290A may be maintained in a locked state to prevent the risk of possibly tainted medicines from being used. Further, the condition and access state may be reported back to medication dispensing console 210 to generate an alert or notification, for example to a nurse, doctor, pharmacy, or other healthcare professional.

Note that while the above process 400 is described with respect to an access command to retrieve a medication, the access command may also be for depositing or adding a new medication. In this case, at block 412, identifying the one or more medications includes the new medications proposed to be added. Block 413 proceeds as usual, but block 414 may determine that the condition of the compartment is unsafe if the current detected temperature range is not safe for the new medications. In this case, block 415 will only provide access to the requested compartment when the temperature reaches a safe range. In this regard, processor 222 may control refrigeration unit 228 to adjust the ambient temperature of compartments 270 until sensor data 232 conforms to the safe temperature range defined by parameters 240.

In some implementations, any of the actions, features or functions of the processor 222 discussed above may be performed by one or more other processors, such as a processor external to the medication dispensing console 210 (e.g., medication dispensing console 140, 210, management server 110). For example, processor 222 may be directed to control and/or monitoring of the medication dispensing console 210 while analysis and determination actions or functions may be handled by one or more external processors. Accordingly, system 100 may include dispensing units 170 that receive commands from a processor external to the dispensing unit 170 and transmit environmental readings (e.g., temperature, light exposure) to that external processor, and may include other dispensing units 170 having an internal processor configured to provide any or all of the external processor functions described above.

Figure 5:
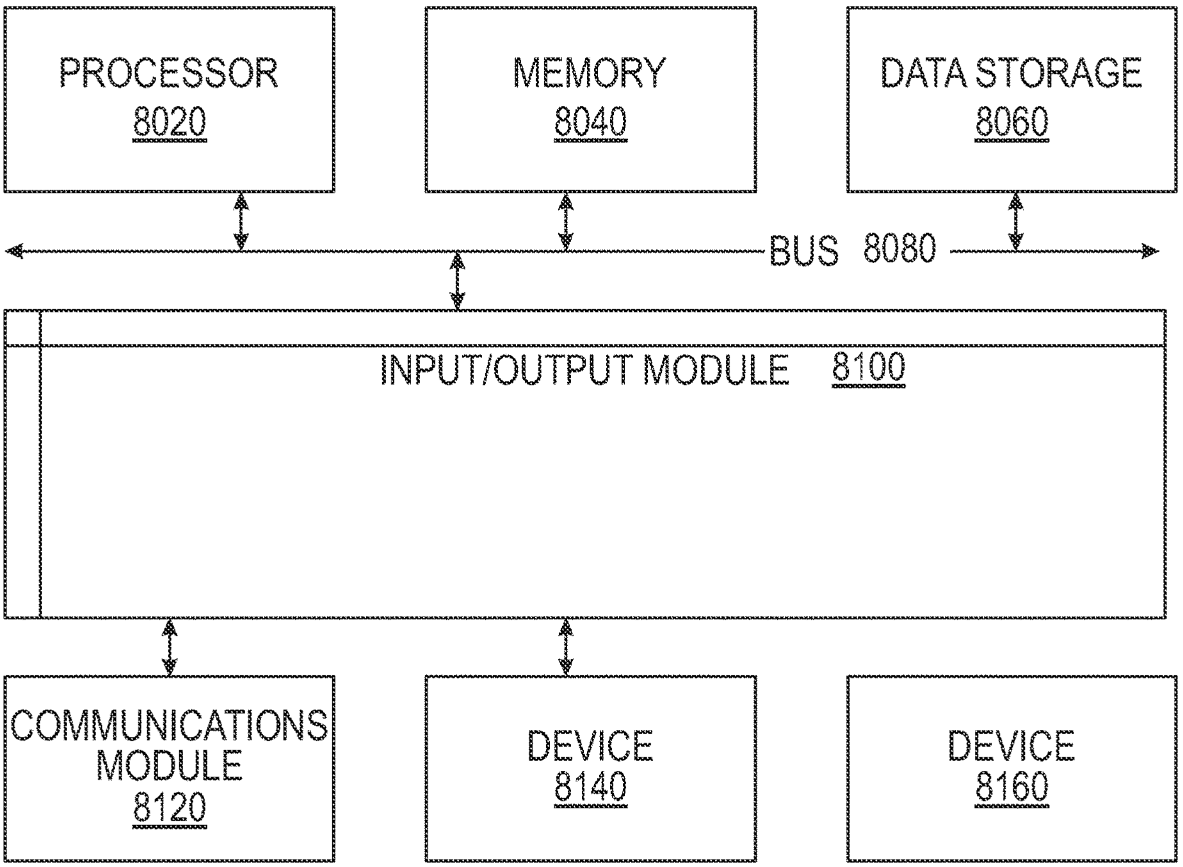
FIG. 5 illustrates an example electronic system, in accordance with one or more implementations.

FIG. 5 conceptually illustrates electronic system 8000 with which one or more implementations of the subject technology may be implemented. Electronic system 8000, for example, can be a medication dispensing device 140, a waste device 150, a server 110, 120, a refrigerator, an ADC, a desktop computer, a laptop computer, a tablet computer, a phone, a personal digital assistant (PDA), or generally any electronic device that transmits signals over a network (e.g., time clocks, proximity badges, biometric identification schemes, and the like). Such an electronic system includes various types of computer readable media and interfaces for various other types of computer readable media. Electronic system 8000 includes bus 8080, processing unit(s) 8120, system memory 8040, read-only memory (ROM) 8100, permanent storage device 8020, input device interface 8140, output device interface 8060, and network interface 8160, or subsets and variations thereof.

Bus 8080 collectively represents all system, peripheral, and chipset buses that communicatively connect the numerous internal devices of electronic system 8000. In one or more implementations, bus 8080 communicatively connects processing unit(s) 8120 with ROM 8100, system memory 8040, and permanent storage device 8020. From these various memory units, processing unit(s) 8120 retrieves instructions to execute and data to process in order to execute the processes of the subject disclosure. The processing unit(s) can be a single processor or a multi-core processor in different implementations.

ROM 8100 stores static data and instructions that are needed by processing unit(s) 812 and other modules of the electronic system. Permanent storage device 8020, on the other hand, is a read-and-write memory device. This device is a non-volatile memory unit that stores instructions and data even when electronic system 8000 is off. One or more implementations of the subject disclosure use a mass-storage device (such as a magnetic or optical disk and its corresponding disk drive) as permanent storage device 8020.

Other implementations use a removable storage device (such as a floppy disk, flash drive, and its corresponding disk drive) as permanent storage device 8020. Like permanent storage device 8020, system memory 8040 is a read-and-write memory device. However, unlike storage device 8020, system memory 8040 is a volatile read-and-write memory, such as random access memory. System memory 8040 stores any of the instructions and data that processing unit(s) 8120 needs at runtime. In one or more implementations, the processes of the subject disclosure are stored in system memory 8040, permanent storage device 8020, and/or ROM 8100. From these various memory units, processing unit(s) 8120 retrieves instructions to execute and data to process in order to execute the processes of one or more implementations.

Bus 8080 also connects to input and output device interfaces 8140 and 8060. Input device interface 8140 enables a user to communicate information and select commands to the electronic system. Input devices used with input device interface 8140 include, for example, alphanumeric keyboards and pointing devices (also called "cursor control devices"). Output device interface 8060 enables, for example, the display of images generated by electronic system 8000. Output devices used with output device interface 806 include, for example, printers and display devices, such as a liquid crystal display (LCD), a light emitting diode (LED) display, an organic light emitting diode (OLED) display, a flexible display, a flat panel display, a solid state display, a projector, or any other device for outputting information. One or more implementations may include devices that function as both input and output devices, such as a touchscreen. In these implementations, feedback provided to the user can be any form of sensory feedback, such as visual feedback, auditory feedback, or tactile feedback; and input from the user can be received in any form, including acoustic, speech, or tactile input.

Also as shown in FIG. 5, bus 8080 also couples electronic system 8000 to a network (not shown) through network interface 8160. In this manner, the computer can be a part of a network of computers (such as a local area network ("LAN"), a wide area network ("WAN"), or an Intranet, or a network of networks, such as the Internet. Any or all components of electronic system 8000 can be used in conjunction with the subject disclosure.

One or more implementations are described in the following concepts.

Concept 1 is a dispensing unit, comprising: one or more sensors, including a temperature sensor; a plurality of compartments, each for storing one or more medicines, wherein at least one of the plurality of compartments is lockable; a lockable door for controlling access to the plurality of compartments; a refrigeration unit for regulating an ambient temperature of the plurality of compartments; and a processor configured to: receive, from a medication dispensing console via a communication interface, an access command for a selected compartment of the plurality of compartments; identifying, responsive to receiving the access command, one or more medications in the selected compartment; determine a safe temperature range of the identified one or more medications; determine, responsive to the received access command, a condition of the selected compartment based on whether sensor data recorded by the one or more sensors conforms to one or more parameters including the safe temperature range; and set, based on the determined condition, an access state of at least one of the selected compartment and the lockable door.

Concept 2 is the dispensing unit of concept 1, wherein the access command comprises retrieving at least one of the one or more medications in the selected compartment.

Concept 3 is the dispensing unit of concept 1, wherein the processor is configured to set the access state of the selected compartment to unlocked when the determined condition indicates the one or more medications are safe and effective to use.

Concept 4 is the dispensing unit of concept 3, wherein the processor is configured to set an access state of one or more other components in a path to the selected compartment to unlocked.

Concept 5 is the dispensing unit of concept 4, wherein the processor is further configured to: confirm a retrieval of at least one of the one or more medications in the selected compartment; and set the access state of the selected compartment and the one or more other components to locked.

Concept 6 is the dispensing unit of concept 3, wherein the processor is configured to maintain an access state of the lockable door to unlocked when the access command is not a final command in an ordered list of access commands received from the medication dispensing console.

Concept 7 is the dispensing unit of concept 1, wherein the processor is configured to maintain the access state of the selected compartment to locked when the determined condition indicates the one or more medications are unsafe or ineffective to use.

Concept 8 is the dispensing unit of concept 1, wherein the processor is further configured to: report at least one of the access state and the condition of the selected compartment to the medication dispensing console via the communication interface to generate an alert or notification.

Concept 9 is the dispensing unit of concept 1, wherein the access command comprises depositing one or more new medications into the selected compartment, and wherein the processor is configured to identify, responsive to receiving the access command, the one or more medications in the selected compartment as including the one or more new medications.

Concept 10 is the dispensing unit of concept 1, wherein the processor is further configured to: regulate the ambient temperature of the plurality of compartments via the refrigeration unit such that the sensor data conforms to the safe temperature range.

Concept 11 is the dispensing unit of concept 1, wherein the processor is further configured to: identify the selected compartment by performing one or more of: illuminating the selected compartment, opening the selected compartment, or moving the selected compartment.

Concept 12 is the dispensing unit of concept 1, wherein the processor is further configured to: prevent closing and locking of the lockable door until an access state of the plurality of compartments is confirmed to be locked.

Concept 13 is the dispensing unit of concept 1, wherein the one or more parameters include safe light exposure of the one or more medications, and wherein the one or more sensors include at least one of a light sensor and a timer for determining a period of time when the lockable door is open.

Concept 14 is a method for providing secure access to refrigerated bins, comprising: receiving, from a medication dispensing console via a communication interface, an access command for a selected compartment of a plurality of compartments, each for storing one or more medicines, wherein at least one of the plurality of compartments is lockable; identifying, responsive to receiving the access command, one or more medications in the selected compartment; determining a safe temperature range of the identified one or more medications; determining, responsive to the received access command, a condition of the selected compartment based on whether sensor data recorded by one or more sensors conforms to one or more parameters including the safe temperature range; and setting, based on the determined condition, an access state of at least one of the selected compartment and a lockable door controlling access to the plurality of compartments.

Concept 15 is the method of concept 14, wherein the access command comprises retrieving at least one of the one or more medications in the selected compartment.

Concept 16 is the method of concept 14, wherein setting the access state of the selected compartment to unlocked is when the determined condition indicates the one or more medications are safe and effective to use.

Concept 17 is the method of concept 14, further comprising: maintaining the access state of the selected compartment to locked when the determined condition indicates the one or more medications are unsafe or ineffective to use.

Concept 18 is the method of concept 14, wherein the access command comprises depositing one or more new medications into the selected compartment, and wherein identifying, responsive to receiving the access command, the one or more medications in the selected compartment further includes the one or more new medications.

Concept 19 is the method of concept 14, further comprising: regulating the ambient temperature of the plurality of compartments via a refrigeration unit such that the sensor data conforms to the safe temperature range.

Concept 20 is a system comprising: means for receiving, from a medication dispensing console via a communication interface, an access command for a selected compartment of a plurality of compartments, each for storing one or more medicines, wherein at least one of the plurality of compartments is lockable; means for identifying, responsive to receiving the access command, one or more medications in the selected compartment; means for determining a safe temperature range of the identified one or more medications; means for determining, responsive to the received access command, a condition of the selected compartment based on whether sensor data recorded by one or more sensors conforms to one or more parameters including the safe temperature range; and means for setting, based on the determined condition, an access state of at least one of the selected compartment and a lockable door controlling access to the plurality of compartments.

Concept 21 is a system, comprising: one or more sensors, including a temperature sensor; a plurality of compartments, each for storing one or more medicines, wherein at least one of the plurality of compartments is lockable; a lockable door for controlling access to the plurality of compartments; a refrigeration unit for regulating an ambient temperature of the plurality of compartments; and a processor configured to: receive, from a medication dispensing console via a communication interface, an access command for a selected compartment of the plurality of compartments; identifying, responsive to receiving the access command, one or more medications in the selected compartment; determine a safe temperature range of the identified one or more medications; determine, responsive to the received access command, a condition of the selected compartment based on whether sensor data recorded by the one or more sensors conforms to one or more parameters including the safe temperature range; and set, based on the determined condition, an access state of at least one of the selected compartment and the lockable door.

Concept 22 is the system of concept 21, wherein the access command comprises retrieving at least one of the one or more medications in the selected compartment.

Concept 23 is the system of concept 21, wherein the processor is configured to set the access state of the selected compartment to unlocked when the determined condition indicates the one or more medications are safe and effective to use.

Concept 24 is the system of concept 23, wherein the processor is configured to set an access state of one or more other components in a path to the selected compartment to unlocked.

Concept 25 is the system of concept 24, wherein the processor is further configured to: confirm a retrieval of at least one of the one or more medications in the selected compartment; and set the access state of the selected compartment and the one or more other components to locked.

Concept 26 is the system of concept 23, wherein the processor is configured to maintain an access state of the lockable door to unlocked when the access command is not a final command in an ordered list of access commands received from the medication dispensing console.

Concept 27 is the system of concept 21, wherein the processor is configured to maintain the access state of the selected compartment to locked when the determined condition indicates the one or more medications are unsafe or ineffective to use.

Concept 28 is the system of concept 21, wherein the processor is further configured to:

report at least one of the access state and the condition of the selected compartment to the medication dispensing console via the communication interface to generate an alert or notification.

Concept 29 is the system of concept 21, wherein the access command comprises depositing one or more new medications into the selected compartment, and wherein the processor is configured to identify, responsive to receiving the access command, the one or more medications in the selected compartment as including the one or more new medications.

Concept 30 is the system of concept 21, wherein the processor is further configured to at least one of: regulate the ambient temperature of the plurality of compartments via the refrigeration unit such that the sensor data conforms to the safe temperature range; and identify the selected compartment by performing one or more of: illuminating the selected compartment, opening the selected compartment, or moving the selected compartment.

Concept 31 is the system of concept 21, wherein a dispensing unit comprises the one or more sensors, the plurality of compartments, the lockable door and the refrigeration unit, and wherein the processor is external to the dispensing unit.

Concept 32 is the system of concept 21, wherein the processor is further configured to: prevent closing and locking of the lockable door until an access state of the plurality of compartments is confirmed to be locked.

Concept 33 is the system of concept 21, wherein the one or more parameters include safe light exposure of the one or more medications, and wherein the one or more sensors include at least one of a light sensor and a timer for determining a period of time when the lockable door is open.

Many of the above-described features and applications may be implemented as software processes that are specified as a set of instructions recorded on a computer readable storage medium (alternatively referred to as computer-readable media, machine-readable media, or machine-readable storage media). When these instructions are executed by one or more processing unit(s) (e.g., one or more processors, cores of processors, or other processing units), they cause the processing unit(s) to perform the actions indicated in the instructions. Examples of computer readable media include, but are not limited to, RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, ultra density optical discs, any other optical or magnetic media, and floppy disks. In one or more implementations, the computer readable media does not include carrier waves and electronic signals passing wirelessly or over wired connections, or any other ephemeral signals. For example, the computer readable media may be entirely restricted to tangible, physical objects that store information in a form that is readable by a computer. In one or more implementations, the computer readable media is non-transitory computer readable media, computer readable storage media, or non-transitory computer readable storage media.

In one or more implementations, a computer program product (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

While the above discussion primarily refers to microprocessor or multi-core processors that execute software, one or more implementations are performed by one or more integrated circuits, such as application specific integrated circuits (ASICs) or field programmable gate arrays (FPGAs). In one or more implementations, such integrated circuits execute instructions that are stored on the circuit itself.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that any specific order or hierarchy of blocks in the processes disclosed is an illustration of example approaches. Based upon design preferences, it is understood that the specific order or hierarchy of blocks in the processes may be rearranged, or that all illustrated blocks be performed. Any of the blocks may be performed simultaneously. In one or more implementations, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The predicate words "configured to", "operable to", and "programmed to" do not imply any particular tangible or intangible modification of a subject, but, rather, are intended to be used interchangeably. In one or more implementations, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as an "aspect" may refer to one or more aspects and vice versa. A phrase such as an "embodiment" does not imply that such embodiment is essential to the subject technology or that such embodiment applies to all configurations of the subject technology. A disclosure relating to an embodiment may apply to all implementations, or one or more implementations. An embodiment may provide one or more examples of the disclosure. A phrase such an "embodiment" may refer to one or more implementations and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as a "configuration" may refer to one or more configurations and vice versa.

The word "exemplary" is used herein to mean "serving as an example, instance, or illustration." Any embodiment described herein as "exemplary" or as an "example" is not necessarily to be construed as preferred or advantageous over other implementations. Furthermore, to the extent that the term "include," "have," or the like is used in the description or the claims, such term is intended to be inclusive in a manner similar to the term "comprise" as "comprise" is interpreted when employed as a transitional word in a claim. Furthermore, to the extent that the term "include," "have," or the like is used in the description or the claims, such term is intended to be inclusive in a manner similar to the term "comprise" as "comprise" is interpreted when employed as a transitional word in a claim.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

Reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

While this specification contains many specifics, these should not be construed as limitations on the scope of what may be claimed, but rather as descriptions of particular implementations of the subject matter. Certain features that are described in this specification in the context of separate implementations can also be implemented in combination in a single embodiment. Conversely, various features that are described in the context of a single embodiment can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The subject matter of this specification has been described in terms of particular aspects, but other aspects can be implemented and are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other variations are within the scope of the following claims.

What is claimed is:

1. A dispensing device, comprising:

a plurality of compartments, each for storing one or more medicines;

a plurality of sensors, each sensor being configured to sense an environmental characteristic of at least one respective compartment of the plurality of compartments;

one or more processors configured to:

receive a request to access a respective compartment of the plurality of compartments;

identify one or more medications stored in the respective compartment;

determine, responsive to receiving the request to access the respective compartment and identifying the one or more medications in the respective compartment, a safe environmental range specific to the identified one or more medications stored in the respective compartment;

determine, responsive to receiving the request to access the respective compartment and identifying the one or more medications, an environmental characteristic of the respective compartment using the sensor configured to sense the environmental characteristic of the respective compartment;

determine whether the determined environmental characteristic of the respective compartment is within the safe environmental range specific to the identified one or more medications; and cause an alert to be displayed when the determined environmental characteristic of the respective compartment is outside of the safe environmental range specific to the identified one or more medications.

2. The dispensing device of claim 1, wherein the sensor is configured to detect light, wherein the safe environmental range comprises a predetermined light exposure threshold, and wherein the one or more processors are configured to cause the dispensing device to:

determine an amount of light exposure associated with the respective compartment based on light detected by the sensor; and determine whether the determined environmental characteristic of the respective compartment is within the safe environmental range based on whether the determined amount of light exposure satisfies the predetermined light exposure threshold.

3. The dispensing device of claim 2, wherein each compartment of the plurality of compartments comprises one or more trays.

4. The dispensing device of claim 1, wherein the one or more processors are further configured to:

receive a selection of a medication for dispense; and identify the respective compartment based on the selection of the medication, the one or more medications stored in the respective compartment comprising the medication for dispense; and receive the request to access the respective compartment after the respective compartment is identified based on the selection.

5. The dispensing device of claim 1, wherein identifying the one or more medications stored in the respective compartment is responsive to receiving the request to access the respective compartment.

6. The dispensing device of claim 1, further comprising:

a lockable door for controlling access to the plurality of compartments, wherein the one or more processors are further configured to:

identify, before receiving the request, a user seeking to access dispensing device; and unlock the lockable door based on the user being authorized to access the dispensing device.

7. The dispensing device of claim 6, wherein the one or more processors are further configured to:

prevent access to the respective compartment, while the lockable door is unlocked, when the sensor measures an environmental characteristic outside of the safe environmental range specific to the identified one or more medications, and provide access to the respective compartment by unlocking the respective compartment when the sensor measures an environmental characteristic within the safe environmental range.

8. The dispensing device of claim 6, wherein the dispensing device further comprises:

a plurality of trays in the dispensing device, the plurality of compartments being within one of the trays, wherein the lockable door controls access to the plurality of trays.

9. The dispensing device of claim 1, wherein the sensor is configured to detect light and wherein the one or more processors are further configured to:

determine, based on an amount of light measured by the sensor for the respective compartment, whether the one or more medications in the respective compartment of the plurality of compartments is safe and effective to use;

cause the respective compartment to be unlocked when the one or more medications in the respective compartment is determined to be safe and effective to use; and cause the respective compartment to be locked when the one or more medications in the respective compartment are not determined to be safe and effective to use.

10. The dispensing device of claim 1, wherein the one or more processors are configured to:

identify the respective compartment by illuminating the respective compartment, opening the respective compartment, or moving the respective compartment.

11. The dispensing device of claim 1, wherein causing the alert to be displayed comprises illuminating the respective compartment.

12. A method for securing a dispensing device, comprising, under control of one or more processors:

receiving a request to access to a respective compartment of a plurality of compartments in a dispensing device, each compartment of the plurality of compartments being associated with a respective environmental sensor, of a plurality of environmental sensors, configured to measure an environmental characteristic of the compartment;

identifying one or more medications stored in the respective compartment;

determining, responsive to receiving the request to access the respective compartment and identifying the one or more medications in the respective compartment, a safe environmental range specific to the identified one or more medications stored in the respective compartment;

measuring, responsive to receiving the request to access the respective compartment and identifying the one or more medications, an environmental characteristic of the respective compartment using the environmental sensor configured to measure the environmental characteristic of the respective compartment;

determining whether the measured environmental characteristic of the respective compartment is within the safe environmental range specific to the identified one or more medications; and causing an alert to be displayed when the measured environmental characteristic of the respective compartment is outside of the safe environmental range specific to the identified one or more medications.

13. The method of claim 12, wherein the environmental sensor is configured to detect light, wherein the safe environmental range comprises a predetermined light exposure threshold, and wherein the method further comprises:

determining an amount of light exposure associated with the respective compartment based on light detected by the environmental sensor; and determining whether the measured environmental characteristic of the respective compartment is within the safe environmental range based on whether the determined amount of light exposure satisfies the predetermined light exposure threshold.

14. The method of claim 12, wherein the method further comprises:

receiving a selection of a medication for dispense; and identifying the respective compartment based on the selection of the medication, the one or more medications stored in the respective compartment being the medication for dispense; and receiving the request to access the respective compartment after the respective compartment is identified based on the selection.

15. The method of claim 12, wherein identifying the one or more medications stored in the respective compartment is responsive to receiving the request to access the respective compartment.

16. The method of claim 12, further comprising:

identifying, before receiving the request, a user seeking to access dispensing device; and unlocking a lockable door based on the user being authorized to access the dispensing device, the lockable door controlling access to the plurality of compartments.

17. The method of claim 16, wherein the method further comprises:

preventing access to the respective compartment, while the lockable door is unlocked, when the environmental sensor measures an environmental characteristic outside of the safe environmental range specific to the identified one or more medications; and providing access to the respective compartment by unlocking the respective compartment when the respective environmental sensor measures an environmental characteristic within the safe environmental range.

18. The method of claim 12, wherein the environmental sensor is configured to detect light and wherein the method further comprises:

determining, based on an amount of light measured by the environmental sensor of the respective compartment, whether the one or more medications in the respective compartment of the plurality of compartments is safe and effective to use;

causing the respective compartment to be unlocked when the one or more medications in the respective compartment is determined to be safe and effective to use; and causing the respective compartment to be locked when the one or more medications in the respective compartment are not determined to be safe and effective to use.

19. The method of claim 12, wherein the method further comprises:

identifying the respective compartment by illuminating the respective compartment, opening the respective compartment, or moving the respective compartment.

20. The method of claim 12, wherein causing the alert to be displayed comprises illuminating the respective compartment.

21. A non-transitory machine readable medium storing instructions thereon that, when executed by one or more processors, cause the one or more processors to perform a method according to claim 12.

22. A dispensing system, comprising:

one or more processors; and a non-transitory machine readable medium storing instructions thereon that, when executed by the one or more processors, cause the one or more processors to perform a method comprising:

receiving a request to access to a respective compartment of a plurality of compartments in a dispensing device, each compartment of the plurality of compartments being associated with a respective environmental sensor, of a plurality of environmental sensors, configured to measure an environmental characteristic of the compartment;

identifying one or more medications stored in the respective compartment;

determining, responsive to receiving the request to access the respective compartment and identifying the one or more medications in the respective compartment, a safe environmental range specific to the identified one or more medications stored in the respective compartment;

measuring, responsive to receiving the request to access the respective compartment and identifying the one or more medications, an environmental characteristic of the respective compartment using the environmental sensor configured to measure the environmental characteristic of the respective compartment;

determining whether the measured environmental characteristic of the respective compartment is within the safe environmental range specific to the identified one or more medications; and causing an alert to be displayed when the measured environmental characteristic of the respective compartment is outside of the safe environmental range specific to the identified one or more medications.

* * * * *